(12) United States Patent
Jin et al.

(10) Patent No.: US 12,158,477 B2
(45) Date of Patent: Dec. 3, 2024

(54) CARTRIDGE CAPABLE OF CENTRIFUGAL SEPARATION AND AUTOMATIC ANALYSIS

(71) Applicant: I-SENS, INC., Seoul (KR)

(72) Inventors: Yungjoon Jin, Seoul (KR); Yusung Kim, Seoul (KR); Kyungho Kim, Seoul (KR); Jae Phil Do, Seoul (KR); Seok-Won Lee, Seongnam si (KR)

(73) Assignee: I-SENS, INC., Seoul (KR)

( * ) Notice: Subject to any disclaimer, the term of this patent is extended or adjusted under 35 U.S.C. 154(b) by 896 days.

(21) Appl. No.: 17/284,958

(22) PCT Filed: Feb. 27, 2019

(86) PCT No.: PCT/KR2019/002364
§ 371 (c)(1),
(2) Date: Apr. 13, 2021

(87) PCT Pub. No.: WO2020/080617
PCT Pub. Date: Apr. 23, 2020

(65) Prior Publication Data
US 2021/0382079 A1  Dec. 9, 2021

(30) Foreign Application Priority Data
Oct. 17, 2018  (KR) .................. 10-2018-0123935

(51) Int. Cl.
*G01N 35/00* (2006.01)
*A61M 1/36* (2006.01)
(Continued)

(52) U.S. Cl.
CPC ......... *G01N 35/025* (2013.01); *A61M 1/3696* (2014.02); *G01N 33/491* (2013.01);
(Continued)

(58) Field of Classification Search
CPC ................................................ G01N 35/025
(Continued)

(56) References Cited

U.S. PATENT DOCUMENTS

| 4,933,147 A | 6/1990 | Hollar et al. |
| 5,011,663 A | 4/1991 | Innocenti |

(Continued)

FOREIGN PATENT DOCUMENTS

| CN | 1890569 B | 3/2011 |
| EP | 2295986 A2 | 3/2011 |

(Continued)

OTHER PUBLICATIONS

Supplementary European Search Report for EP Application No. 19872769 (The Hague) completed Jun. 1, 2022 (7 pages).

(Continued)

*Primary Examiner* — Christine T Mui
*Assistant Examiner* — Emily R. Berkeley
(74) *Attorney, Agent, or Firm* — ALSTON & BIRD LLP

(57) ABSTRACT

A cartridge capable of a centrifugation and an automatic analysis according to an embodiment of the present invention includes: at least two or more sample wells, a centrifugation well, a measuring well, and a tip receiving well, in which a container is formed into a lower portion along a circumference of a circular plate with a predetermined interval, wherein the centrifugation well is sealed with one lid paper along with at least two or more of the sample wells, a blood injection unit is further formed inside of a radius direction for the centrifugation well, the blood injection unit has an outer blood injection hole formed to be spaced inside the centrifugation well in the radius direction, an inclined passage that communicates with the centrifugation well (Continued)

from the outer blood injection hole, and a cover integrally attached to the outer blood injection hole to open and close the blood injection hole.

6 Claims, 7 Drawing Sheets

(51) Int. Cl.
    *G01N 33/49*     (2006.01)
    *G01N 35/02*     (2006.01)

(52) U.S. Cl.
    CPC .............. *G01N 2035/00287* (2013.01); *G01N 2035/00326* (2013.01); *G01N 2035/00495* (2013.01)

(58) Field of Classification Search
    USPC ........................................................ 436/177
    See application file for complete search history.

(56) References Cited

U.S. PATENT DOCUMENTS

| | | |
|---|---|---|
| 5,035,861 A | 7/1991 | Grandone |
| 5,149,501 A | 9/1992 | Babson et al. |
| 5,256,376 A | 10/1993 | Callan et al. |
| 5,919,711 A | 7/1999 | Boyd et al. |
| 7,749,722 B2 | 7/2010 | Okamura et al. |
| 8,287,823 B2 | 10/2012 | Sellers et al. |
| 8,383,421 B2 | 2/2013 | Yanagida et al. |
| 2010/0086990 A1 | 4/2010 | Stanley et al. |
| 2011/0093207 A1 | 4/2011 | Ingber et al. |
| 2012/0202673 A1 | 8/2012 | Runyon et al. |
| 2017/0014823 A1 | 1/2017 | Bru Gibert et al. |
| 2017/0292967 A1 | 10/2017 | Kim et al. |

FOREIGN PATENT DOCUMENTS

| | | |
|---|---|---|
| KR | 10-2004-0062657 A | 7/2004 |
| KR | 10-2015-0104569 A | 9/2015 |
| KR | 10-2016-0018200 A | 2/2016 |
| KR | 10-2016-0114494 A | 10/2016 |
| KR | 10-2016-0148482 A | 12/2016 |
| KR | 10-2017-0002505 A | 1/2017 |
| KR | 10-2017-0115692 A | 10/2017 |
| KR | 10-2018-0106756 A | 10/2018 |

OTHER PUBLICATIONS

Hisato Oka, "Specifications and new functions of the acute care system AQT90 FLEX", Journal of Analytical Bio-Science, vol. 37, No. 2, pp. 109-114, 2014.

International Search Report for PCT/KR2019/002364 (ISA/KR) dated Jul. 16, 2019 (3 pages).

Written Opinion for PCT/KR2019/002364 (ISA/KR) dated Jul. 16, 2019 (5 pages).

# CARTRIDGE CAPABLE OF CENTRIFUGAL SEPARATION AND AUTOMATIC ANALYSIS

CROSS-REFERENCE TO RELATED APPLICATIONS

The present application is a national phase entry of International Application No. PCT/KR2019/002364, filed Feb. 27, 2019, which claims priority to Korean Patent Application No. 10-2018-0123935, filed Oct. 17, 2018, which are incorporated herein by reference in their entirety.

TECHNICAL FIELD

The present invention relates to a cartridge capable of a centrifugation and an automatic analysis. More particularly, the present invention relates to a cartridge that is equipped in an automatic analysis device to separate blood into red blood cells and plasma without contamination and automatically analyze them, thereby being capable of centrifugation and automatic analysis.

BACKGROUND ART

Conventionally, automatic analysis devices for measuring components in biological samples such as blood samples and urine samples have been mainly used to measure biochemical items such as enzymes. However, in recent years, measurements of immunological items such as hormones and tumor markers are also increasing. In the biochemical automatic analysis device, in general, absorbance of a reaction solution is changed due to a biochemical reaction in a blood sample, and a material to be tested is measured by transmitted light and scattered light.

On the other hand, in a serum automatic analysis device for immunological items, after reacting immunologically with a material to be tested in the sample, an antibody or an antigen labeled with a fluorescent dye, etc. with an antibody or antigen that specifically binds to each material to be tested prepared as a reagent, B/F separation is performed, and the material to be tested such as hormones in a biological material with high sensitivity is measured by a heterogeneous measurement for detecting the labeled antibody or the labeled antigen.

Here, the B/F separation means separating a binding component (Bind; B) to be analyzed and a free component (Free; F) that is not to be analyzed.

In addition, immunoassay measurement equipment measures a concentration of a specific biomarker protein in human plasma or serum, and when the plasma or the serum is directly used as a measurement sample, it is not necessary to correct the measurement concentration, but when using blood, the measurement concentration must be corrected by using a volume ratio of red blood cells of the sample.

Therefore, most of the existing equipment must input the volume ratio of the red blood cells or the sample type (blood/plasma/serum), which are separately measured externally, to the equipment.

In other words, most conventional automatic analysis devices are used by separating the blood into red blood cells and plasma in advance, or because the number of the red blood cells of the subject should be input to the automatic analysis device, it is not only cumbersome, but also there is a problem that accuracy of the test is poor in some cases.

DISCLOSURE

Technical Problem

The present invention is devised to solve these problems, and the object of the present invention is to provide a cartridge capable of centrifugation and automatic analysis by centrifuging blood with red blood cells and plasma in an automatic analysis device and then automatically analyzing them directly, such that there is no need for individual input by a tester, accuracy of a measurement may be increased, and even if a design is down-sized and optimized and then be extended by being combined in a modular way, a size of an entire system may be reduced, and diagnosis may be achieved in a shortest time for various items or various diseases.

Particularly, the object of the present invention is to provide a cartridge capable of centrifugation and automatic analysis, in which centrifugation performance is improved during high-speed rotation, occurrence of vibration or noise may be reduced, and in which blood may be prevented from escaping and contaminating the outside during the centrifugation, a design of centrifugation is well optimized to enable automatic pipetting may be provided, and a closing after inputting the blood in the centrifuge well may be not forged.

Technical Solution

A cartridge capable of centrifugation and automatic analysis according to an embodiment of the present invention includes at least two or more sample wells, a centrifugation well, a measuring well, and a tip receiving well, in which a container is formed into a lower portion along a circumference of a circular plate with a predetermined interval, wherein the centrifugation well is sealed with one lid paper along with at least two or more of the samples of the well, and a blood injection unit is further formed inside of a radius direction for the centrifugation well, the blood injection unit has an outer blood injection hole formed to be spaced inside the centrifugation well in the radius direction, and an inclined passage that communicates with the centrifugation well from the outer blood injection hole and a cover integrally attached to the outer blood injection hole to open and close the blood injection hole.

Advantageous Effects

When using the cartridge capable of the centrifugation for automatic analysis according to an embodiment of the present invention, by separating the blood into the red blood cells and the plasma in the automatic analysis device and performing the automatic analysis directly, an individual input of the tester is not required, measurement accuracy may be improved, and the design is down-sized and optimized so that, even if multiple units may be combined and expanded as a module type, the size of the entire system may be reduced, and a diagnosis for various items or diseases may be made in the shortest time.

When using the cartridge capable of the centrifugation for automatic analysis according to an embodiment of the present invention, the centrifugation performance may be improved during high-speed rotation, generation of vibration or noise may be reduced, the blood may be prevented from escaping and contaminating the outside during the centrifugation, and the optimized centrifugation well may be provided to enable automatic pipetting, and in addition, a closing after injecting the blood into the centrifugation well may be not forget.

When using the cartridge capable of the centrifugation for automatic analysis according to an embodiment of the present invention, in the process of the centrifugation, weight balancing is well performed, so that the centrifugation is completed accurately, and the plasma and the blood cells are completely separated, so that accuracy of the automatic measurement may be improved.

When using the cartridge capable of the centrifugation for automatic analysis according to an embodiment of the present invention, even when the cartridge is rotated at a high speed for the centrifugation, blood escaping and contaminating the inside of the peripheral device or other wells may be prevented.

When using the cartridge capable of the centrifugation for automatic analysis according to an embodiment of the present invention, for the automatic analysis after the centrifugation, when punching an air foil of a lid paper covered on the cartridge by using the tip disposed on the cartridge, only the plasma may be accurately pipetted without air leakage, therefore not contaminating the surrounding area or pipetting the blood cells and the plasma together.

When using the cartridge capable of the centrifugation for automatic analysis according to an embodiment of the present invention, when injecting the blood into the centrifugation well, there is no blood that falls vertically into the centrifugation well and bounces around to be contaminated or inconvenience that it should be closed with an air foil or a stopper after the blood is injected, the blood may be prevented from escaping and damaging the entire equipment even when the centrifugation well is not accidentally closed.

MODE FOR INVENTION

Figure 1:
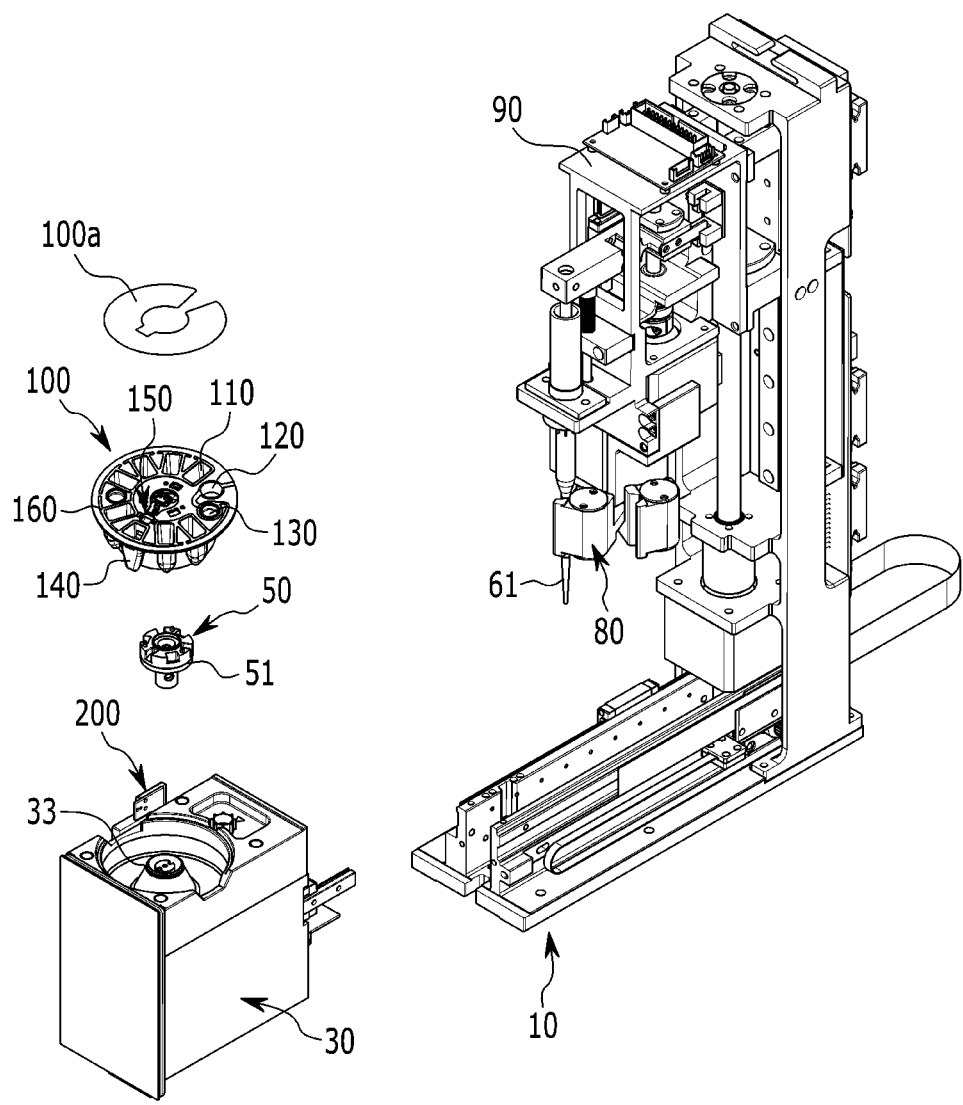
FIG. 1 is an exploded perspective view of a module type of automatic analysis device having a cartridge capable of centrifugation and automatic analysis according to an embodiment of the present invention.

In the following detailed description, only certain embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

Throughout the specification, unless explicitly described to the contrary, the word "comprise", and variations such as "comprises" or "comprising", will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Now, an automatic analysis device having a cartridge capable of a centrifugation and an automatic analysis according to an embodiment of the present invention is described with reference to accompanying drawings.

As shown in FIG. 1, in an automatic analysis device 1 having a cartridge 100 capable of centrifugation and automatic analysis according to an embodiment of the present invention, the cartridge 100 capable of the centrifugation and the automatic analysis may be accommodated in a cartridge receiving housing 30 taken out from an exterior housing by an X-axis transferring unit 20 capable of reciprocating a main body frame 10 disposed on the bottom of the exterior housing in the X-axis direction, and may be again disposed on the main body frame 10. The cartridge receiving housing 30 may have a receiving chamber 33 therein.

The cartridge 100 capable of the centrifugation and the automatic analysis is rotatably connected to the rotation driving unit 50 installed in the cartridge housing 30, thereby being rotated at a high speed for the centrifugation or moved turning at a predetermined interval.

A tip 61 injects a sample for the cartridge 100 capable of the centrifugation and the automatic analysis by a tip elevating unit 60 disposed on the main body frame 10, so it is possible to perform an analysis process such as mixing and washing by performing a repeated operation of a suction/discharge of a reagent.

The measuring unit 70 operates the rotation driving unit 40 according to an automatic analysis program of an immunity, etc., thereby centrifuging the sample (the blood) contained in the cartridge 100 capable of the centrifugation and the automatic analysis and measuring the reaction between the reagent and the sample.

A Z-axis driving unit 90 reciprocates the tip elevating unit 60 and the measuring unit 70 in the Z-axis direction for the main body frame 10, and each constituent element of the automatic analysis device 1 may be controlled by a controlling unit C so that the centrifugation and the automatic analysis for one cartridge may be carried out.

The tip 61 may be coupled to be attachable/detachable to the tip elevating unit 60 in a variety of ways and may perform a suction of the quantification of the reagent from one well/a displacement to another wall to be discharged and a reagent scenario therefor under the control of the controlling unit C.

The measuring unit 70 uses detection methods that are commonly used, such as fluorescence measurement, chemiluminescence enzyme immunoassay analysis (CLEIA), time resolved fluorescence (TRF), and absorbance measurement, thereby performing detection of reaction on the cartridge 100 capable of the centrifugation and the automatic analysis.

An additional magnetron 80 may be installed near the measuring unit 70, which generates and irradiates microwaves to add chemiluminescent substrates to immune complexes. In this case, the measuring unit 70 may include an optical amplification device that measures light emission.

Figure 2:
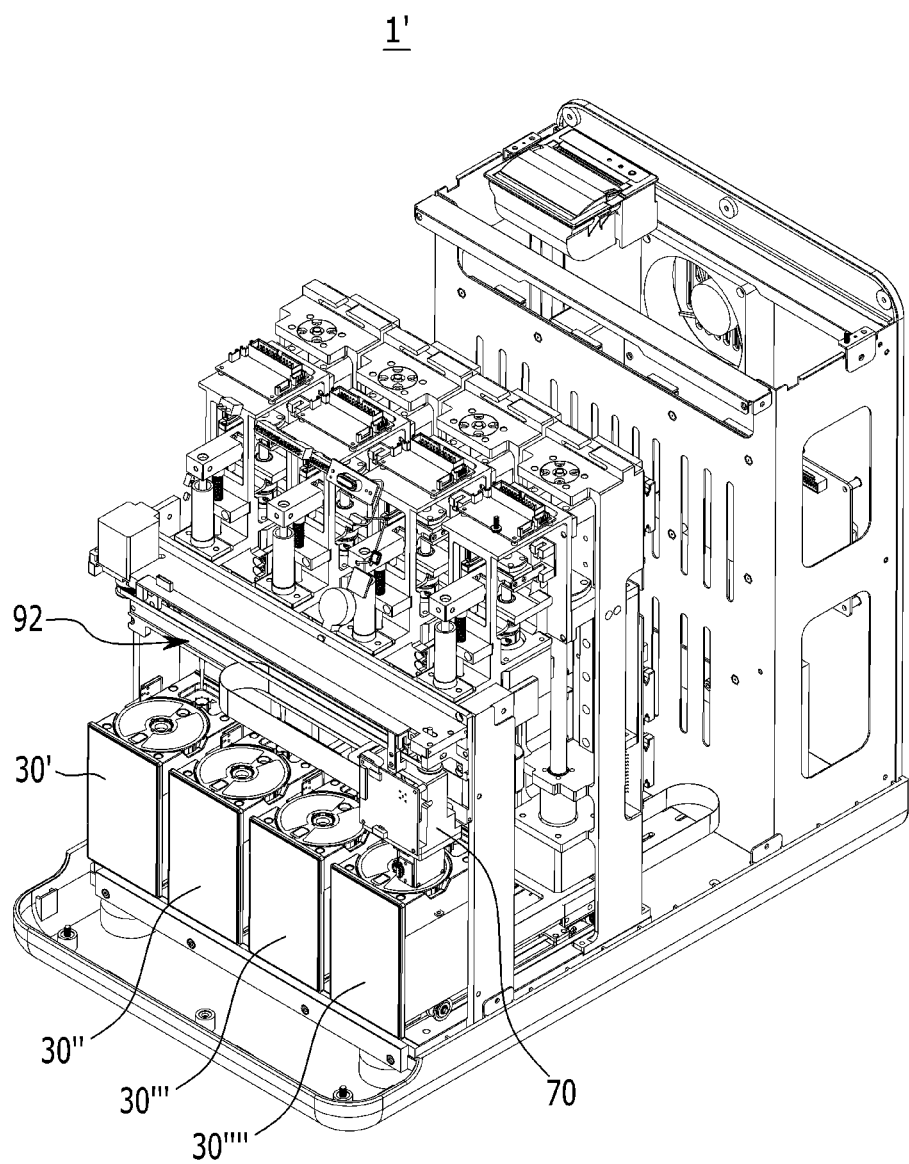
FIG. 2 is an exploded perspective view showing an extended type of a module type of automatic analysis device having a cartridge capable of centrifugation and automatic analysis according to an embodiment of the present invention.

As shown in FIG. 2, at least two or more automatic analysis devices 1' having the cartridge 100 capable of the centrifugation and the automatic analysis according to an embodiment of the present invention may be installed side by side in the Y-axis direction and used.

At this time, at least two or more cartridge receiving housings 30 may be installed in one outer housing, and may be independently taken out through a door formed in the one outer housing and may be again inserted into the outer housing after the cartridge 100 capable of the centrifugation and the automatic analysis is installed.

Of course, for the cartridge receiving housing 30, the tip 61, the tip elevating unit 60, the measuring unit 70, and the magnetron 80 may be configured to correspond one by one to each other.

In addition, a Y-axis direction transferring unit 92 in a form of a belt may be further provided so that the tip elevating unit 60 and the measuring unit 70 are used in cartridge receiving housings 30', 30'', 30''', and 30'' disposed adjacent into the Y-axis direction when the centrifugation is being performed for the cartridge 100 in the outer housing.

As such, the automatic analysis device 1 having the cartridge 100 capable of the centrifugation and the automatic analysis according to an embodiment of the present invention may be easily extended into a module type design so as to respond to various market conditions, may be easily after-serviced (A/S), and may improve spatial utility by a compact size.

In addition, the automatic analysis device 1 having the cartridge 100 capable of the centrifugation and the automatic analysis according to an embodiment of the present invention is individually driven and may be advantageous for emergency treatment when multiple units are installed, an analysis time is advantageous for the emergencies at within 15 minutes, and the centrifugation may be performed within each automatic analysis device 1, which may improve analysis correlation between the plasma/blood cells and increase measurement precision.

Next, the cartridge 100 capable of the centrifugation and the automatic analysis according to an embodiment of the present invention is described in detail with reference to FIG. 3 to FIG. 7.

As shown in FIG. 3 to FIG. 7, the cartridge 100 capable of the centrifugation and the automatic analysis according to an embodiment of the present invention includes a center hole 101a to which the rotation driving unit 50 is coupled at the center of the circular plate 101 and at least two or more sample wells 110, and a measuring well 120, a reagent well 130, and a centrifugation well 140, in which a container is formed downward at a regular interval along the outer circumference part of the center hole 101a.

In the lower part of the circular plate 101, a cylinder-shaped supporting plate 103 is further formed to connect and support at least two or more of the sample well 110, the measuring well 120, the reagent well 130, and the centrifugation well 140.

The reagent or water for washing may be bottled in at least two or more of the sample wells 110, a fluorescent material for injection into at least two or more sample wells 110 in which the reagent and the plasma separated from the blood described later are mixed may be bottled in the measuring well 120, the reagent including the fluorescent material may be bottled in the reagent well 130, and the blood may be injected into the centrifugation well 140 to allow centrifugation of the blood into the plasma and the blood cells during high-speed rotation by the rotation driving unit 50.

Figure 3:
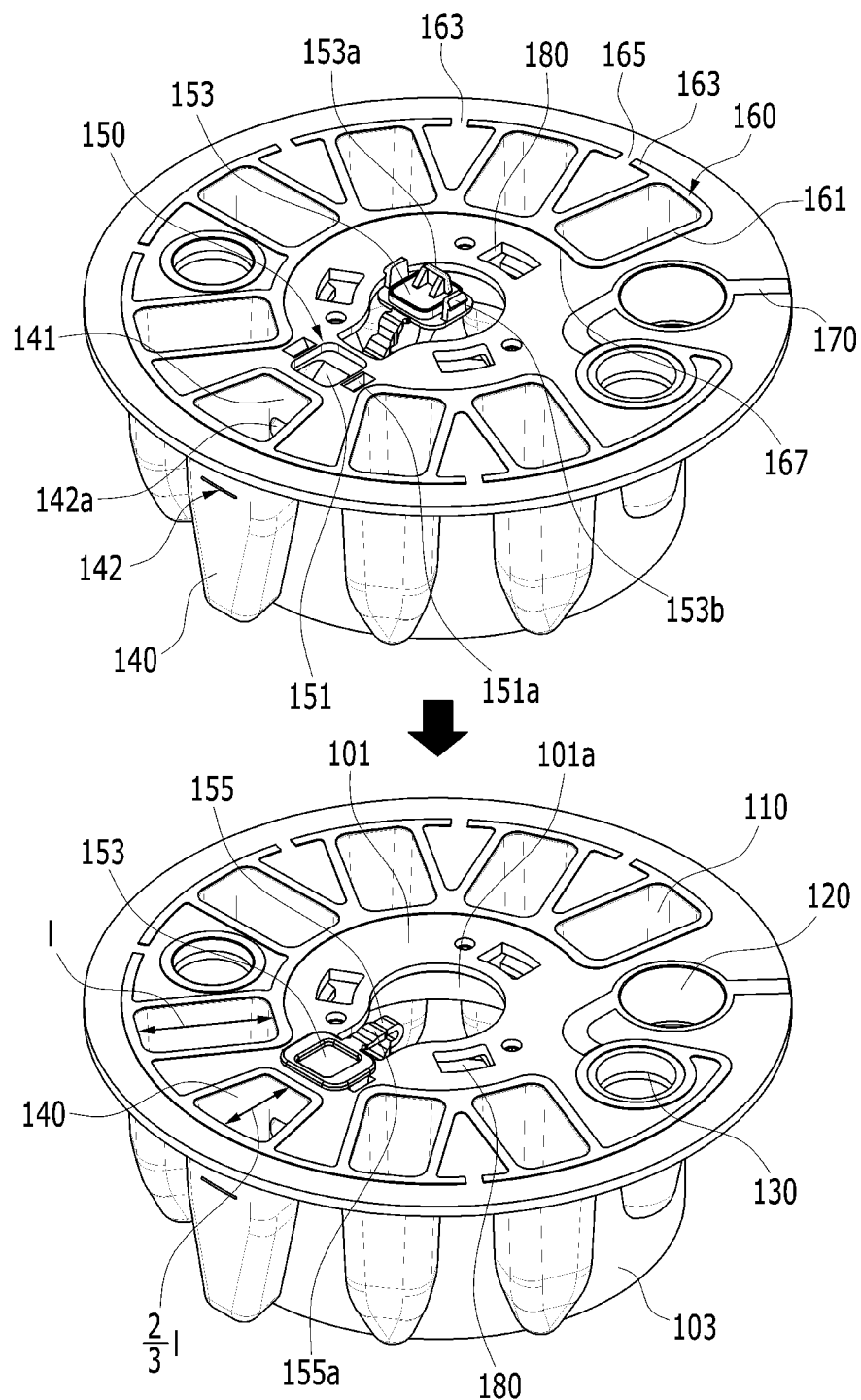
FIG. 3 is a conceptual perspective view explaining a configuration and a usage method of a cartridge capable of centrifugation and automatic analysis according to an embodiment of the present invention.

As shown in FIG. 3, at least two or more sample wells 110 have a rectangle cross-section extended long in the radius direction, the centrifugation well 140 has ⅔ l length of the long side l of at least two or more sample wells 110, the exterior circumference side thereof has a longer trapezoidal cross-section compared to the inner circumference side thereof, and the reagent well 130 has a circular cross-section, but is configured to be narrower toward the bottom.

At least two or more of the sample wells 110, the reagent well 130, and the centrifugation well 140 are structured to become narrower toward the bottom, so that they are structurally durable and stable, and even if the samples are small, automatic pipetting may be possible.

On the other hand, a blood injection unit 150, which may inject the blood for the centrifugation well 140 without a surrounding contamination, is spaced and disposed with a predetermined interval inside the radius direction of the centrifugation well 140.

In this way, since the centrifugation well 140 and the blood injection unit 150 are disposed to be spaced with a predetermined interval, the blood injection unit 150 inserts a pipette tip 152 into the inclined passage obliquely formed between the outer blood injection hole and the inner blood injection hole 141a formed on the inner wall 141 of the centrifugation well 140, thereby securely injecting the blood sample into the centrifugation well 140.

The blood injection unit 150 includes a cover 153 that is integrally attached to the outer blood injection hole to open and close the outer blood injection hole 151.

The cover 153 has a strip 155 that extends in the radius direction of the outer blood injection hole and a corrugated part 155a formed in the transverse direction on the strip 155, and is further provided with a reinforcing lip 153a inserted into the outer blood injection hole on the inside thereof and a coupling lip 153b that is coupled to the coupling hole 151a formed on the left and right sides of the outer blood injection hole.

The cover 153 may maintain a predetermined shape for the outer blood injection hole through the strip 155 on which the corrugated part 155a is formed, so that the closed state may be maintained after being closed and maintained in the center hole 101a so as to not be disturbed even when the blood is injected into the outer blood injection hole.

The cover 153 covers the outer blood injection hole deeper by the reinforcing lip 153a and the coupling lip 153b to completely prevent the blood from escaping or leaking during the centrifugation, and may avoid losing the cover or forgetting the covering of the outer blood injection hole.

Also, since the centrifugation well 140 and the blood injection unit 150 are separated, the centrifugation well 140 may be simultaneously covered with a lid paper 100a such as an air foil along with at least two or more of the sample well 110, the fluorescent material well 120, and the tip receiving well 130.

According to this configuration, in the state that the cover 153 is opened and maintained in the opened state, by flowing the blood into the inner blood injection hole 141a formed as the inner wall 141 of the centrifugation well 140 along the inclined passage though the outer blood injection hole by using the pipette tip 152, it is possible to prevent the blood from splashing and contaminating the surrounding area.

Figure 5:
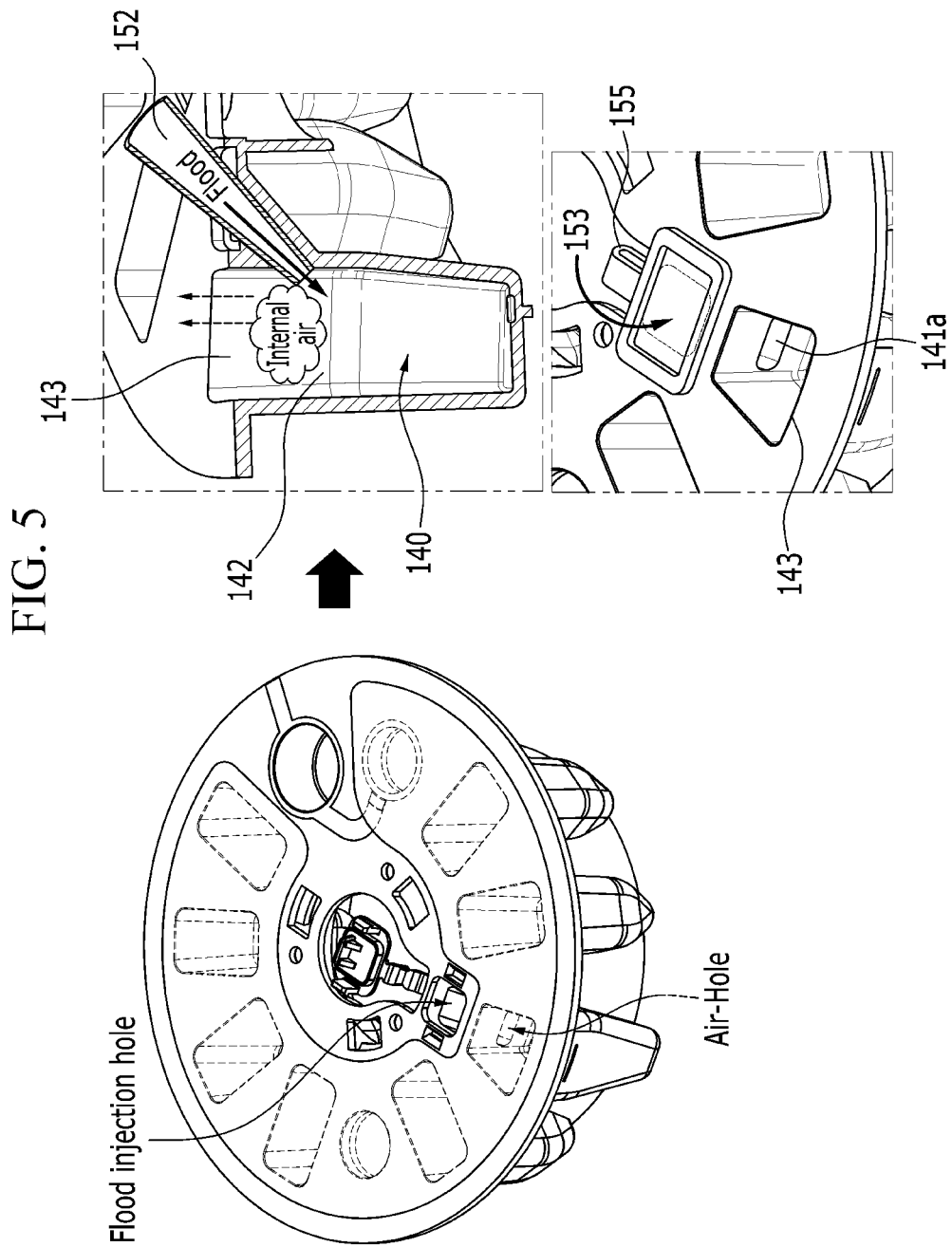
FIG. 5 is a view illustrating a configuration of a cartridge capable of centrifugation and automatic analysis according to an embodiment of the present invention.

In addition, when the blood is injected vertically for the centrifugation well 140, the splattered blood not only contaminates the surroundings, but also prevents the internal air from escaping, but as in the present invention, by injecting the blood into the outer blood injection hole, the internal air 143 of FIG. 5 may escape through the air hole of the air foil of the centrifugation well 140, so the blood may be prevented from contaminating the surroundings by the positive pressure inside the well 140 during the pipetting, which is described later.

Figure 4:
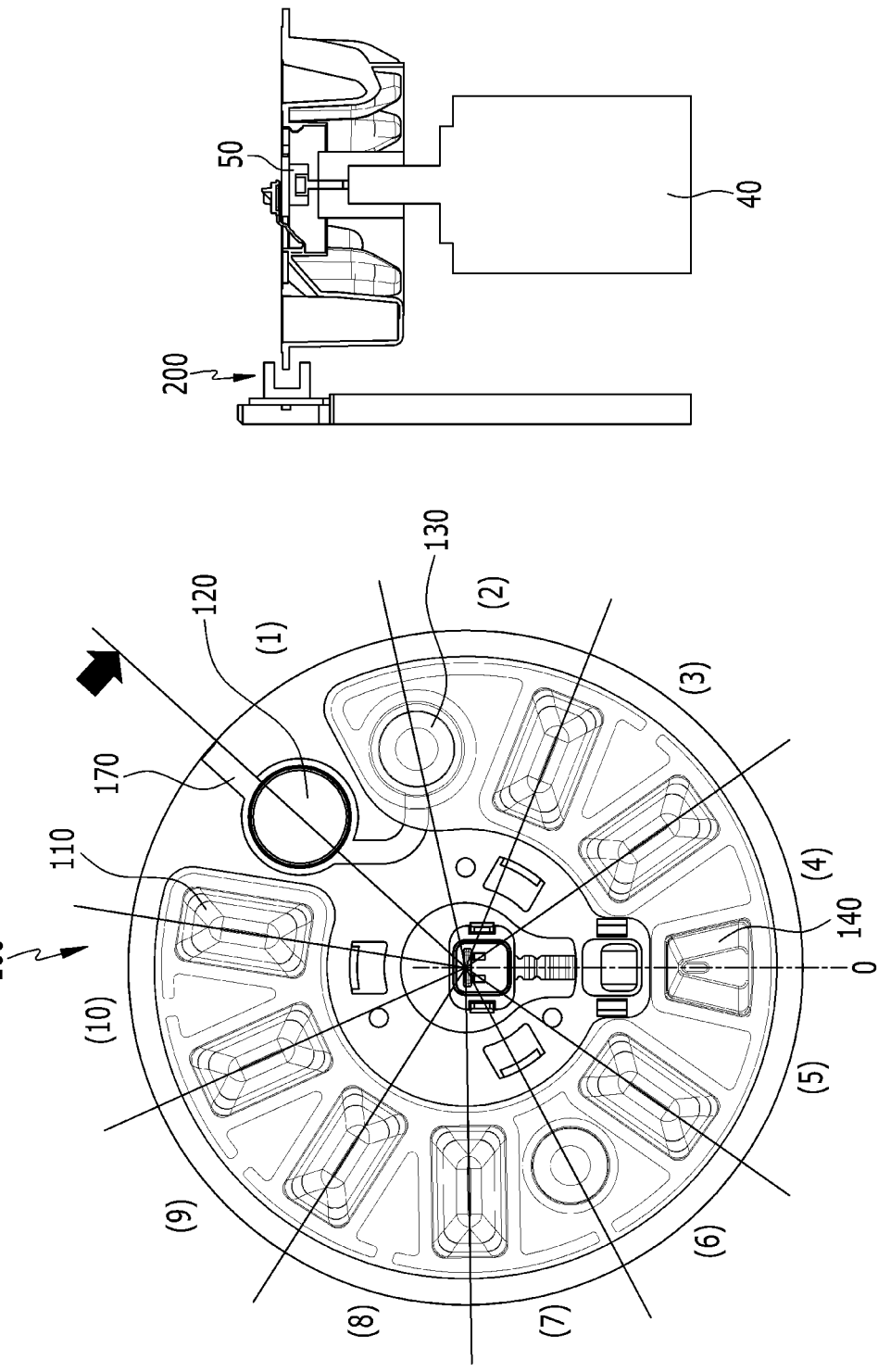
FIG. 4 is a view for explaining an origin mark and weight balancing of a cartridge capable of centrifugation and automatic analysis according to an embodiment of the present invention.

As shown in FIG. 4, in the cartridge 100 capable of the centrifugation and the automatic analysis according to an embodiment of the present invention, as described above, a sealing edge unit 160 may be further provided so that the tip part 61 may accurately and easily pipet the desired point of the lid paper 100a without damaging other areas during the pipetting even if the centrifugation well 140 is simultaneously covered with the lid paper 100a such as the air foil like at least two or more sample wells 110, the fluorescent material well 120 and the tip receiving well 130.

The sealing edge unit 160 independently wraps at least two or more of the sample well 110, the reagent well 130, and the centrifugation well 140 to form a jaw on the upper part of the circular plate 101 to be isolated, thereby preventing the contamination from each other and easily and well bonding the lid paper 100a by heat fusion.

The sealing edge unit 160 includes an edge part 161 independently wrapping at least two or more sample wells 110, the reagent well 130 and the centrifugation well 140 and connected to each other, a spaced edge part 163 spaced with a predetermined distance along the exterior circumference part of the circular plate 101 among the edge part 161 and an air outlet 165 formed between the spaced edge parts 163.

Even if the lid paper 100a consists of one sheet, each of the wells 110, 120, 130, and 140 connected with an inner integrated sealing edge part 167 may be isolated when pipetting by the edge part 161, and the internal air is discharged by the air outlet 165, thereby solving problems that the lid paper 100a is creased or separated.

On the other hand, as shown in FIG. 4, if the cartridge 100 for the centrifugation and simultaneous automatic analysis is loaded into the cartridge housing 30, to automatically check whether it is disposed on any position among a test position of the tip 61 in which the sample test is performed and mounting or detachment positions of the tip 61 before the starting or after the ending of the sample test start, an origin mark 170 is provided on the circular plate 101, and the origin point may be automatically adjusted by irradiating light from a position sensor 200 installed along the side well of the cartridge housing 30 and confirming the origin mark 170.

Accordingly, it is possible to clearly know the start and end time of the sample test process and prevent the measuring unit 70 or the magnetron 80 from being operated at the mounting and detachment positions of the tip 61.

In addition, in the cartridge 100 capable of the centrifugation and the automatic analysis, at least two and preferably three coupling grooves 180 that are coupled with a coupling protrusion 51 of the rotation driving unit 50 to prevent the separation from the rotation driving unit 50 even when rotating at high speed may be installed around the center hole.

Again, referring to FIG. 4, in the cartridge 100 capable of the centrifugation and the automatic analysis according to an embodiment of the present invention, it is explained that the weight balancing is performed even during the high-speed rotation of the rotation driving unit 50, so that centrifugation is well performed, and vibration and noise are greatly reduced during the rotation.

In general, among at least two or more of the sample wells 110, only at least 1 or more may store the reagent, a buffer, and a washing solution, and at least 1 or more may store the plasma extracted from the centrifugation well 140 or be empty to measure the immune reaction.

Therefore, the weight balancing is not performed and the centrifugation is not performed properly, or only the vibration and noise occur.

However, in the cartridge 100 for the centrifugation and simultaneous automatic analysis according to an embodiment of the present invention, the reagent, the buffer, and the washing solution are selectively contained in at least two or more of the sample wells 110 so that eleven mass center lines are formed based on the mass center of the centrifugation well 140.

In the cartridge 100 capable of the centrifugation and the automatic analysis according to an embodiment of the present invention, at least two or more of the sample well 110, the fluorescent material well 120, and the tip receiving well 130 are disposed so that the weight balancing is formed based on the mass center of the centrifugation well 140 from the design. By deriving an optimal simulation (X=0 and Y=0) of a 3D design, the mass center is matched.

Therefore, it further has a balancing display unit 142 that displays the height of the blood to be injected into the centrifugation well 140 so that the blood corresponding to the total weight of the reagent, the buffer, and the washing solution selectively contained in at least two or more of the sample wells 110 is injected into the centrifugation well 140.

The balancing display unit 142 is preferably disposed under the blood injection hole 142a formed on the inner wall 141 of the centrifugation well 140 to prevent a backflow or splashing of the blood.

Experimental Example 1

After injecting the blood into the centrifugation well 140, the total amount of the reagent, the buffer, and the washing solution is distributed for (1) to (11), and then the rotation driving unit 50 is centrifuged at 4000 rpm for 2 minutes according to the weight balancing of each area, and the noise and vibration existence in the centrifugation state were tested.

TABLE 1

| | 1 balancing (X = 0.1/Y = 0.1 or more) | 2 balancing (X = 0.1/Y = 0.1 or less) |
|---|---|---|
| Vibration state | vibration occurrence | Vibration very stable |
| Vibration acceleration (m/s²) | 9.0 ↑ | 0.4 ↓ |

Figure 6:
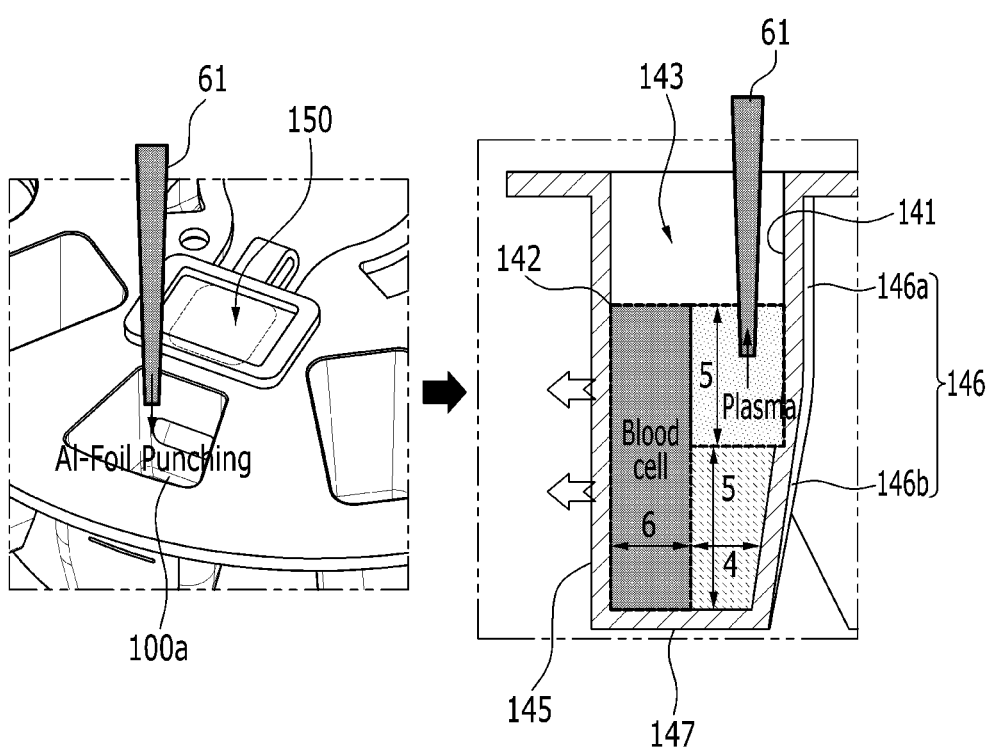
FIG. 6 is a view explaining a design for automatic pipetting of a cartridge capable of centrifugation and automatic analysis according to an embodiment of the present invention.

As shown Table 1, as eleven well weight balancing are closer to X=0 and Y=0 based on the center of the centrifugation well 140, it may be confirmed that the vibration and the noise hardly occur. As shown in FIG. 6, the centrifugation well 140 is designed so that the tip 61 punches the lid paper 100a on the circular plate 101 and then automatically pipets only the required plasma accurately.

That is, since a phenomenon that the heavier blood cells are displaced in the outer section part 145 of the centrifugation well 140 by the centrifugal force during high-speed rotation for the centrifugation and the lighter plasma is disposed in the inner section part 146 of the centrifugation well 140, and hepa torclet (the blood cells) in the blood are occupied in about a 40 to 60% range, the outer section part 145 and the inner section part 146 are present at about a 6:4 ratio based on the diameter of the bottom part 147 so that the plasma may be easily pipetted, the outer section part 145 forms a vertical outer wall and the inner section part 146 forms a vertical section part 146a for the upper part for easy access of the tip part 61, and the plasma may be pushed up to one side of the upper part so that only the plasma may be separated by the automatic pipetting by installing an inclined section 146b inclined to the outside of the radius direction with a ratio of 5:5 so that the plasma, which is less segregated, comes at the lower part.

Figure 7:
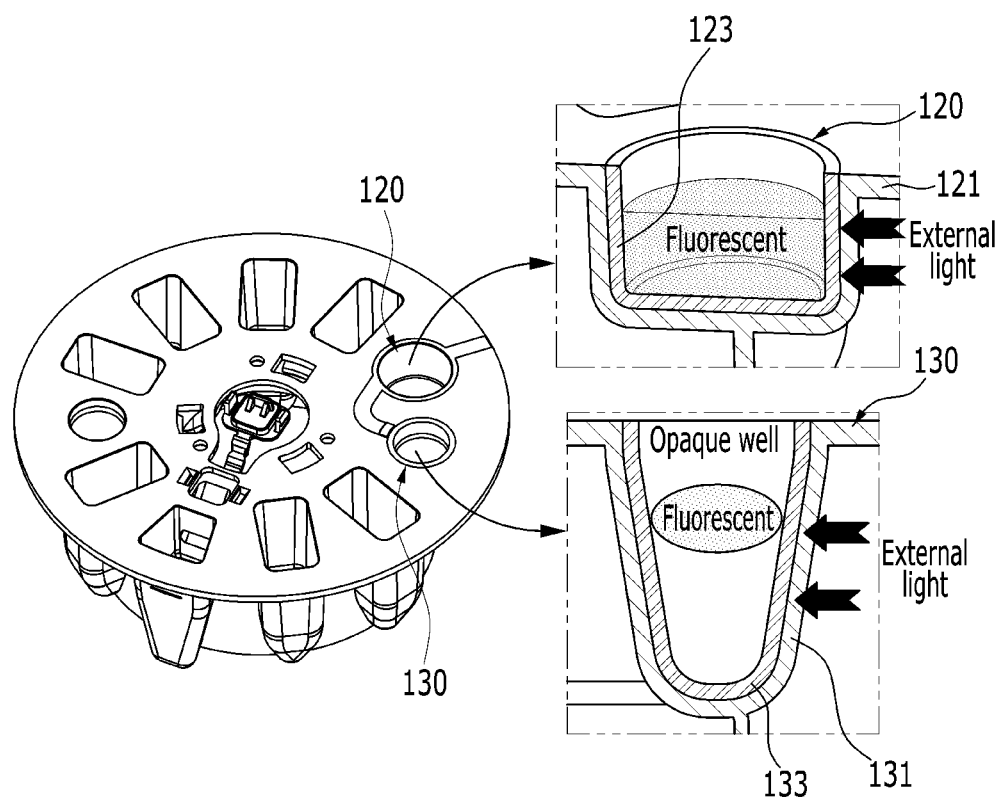
FIG. 7 is a view illustrating a configuration of a measuring well of a cartridge capable of centrifugation and automatic analysis according to an embodiment of the present invention.

On the other hand, as shown in FIG. 7, in the cartridge 100 for the centrifugation and simultaneous automatic analysis according to an embodiment of the present invention, opaque sections 123 and 133 are formed for the wall parts 121 and 131 at the wells 120 and 130 where the fluorescent material is used as one among at least two or more of the wells 110, 120, and 130, thereby the internal fluorescent material may be protected by blocking external light.

The invention claimed is:

1. A cartridge capable of centrifugation and automatic analysis, in which centrifugation is performed by being installed on a main body frame that may be taken out in one direction for an automatic analysis device and automatic analysis is performed using a tip that is movable up and down directly on the main body frame, comprising:
   at least two or more of a sample well, a centrifugation well, a measuring well, and a tip receiving well, which are respectively formed into a lower portion along a circumference of a circular plate with a predetermined interval,
   wherein one lid paper seals the centrifugation well and at least two or more of the sample wells,
   a blood injection unit is further formed inside of a radius direction for the centrifugation well, and
   the blood injection unit has an outer blood injection hole formed inside of the centrifugation well in the radius direction, an inclined passage that communicates with the centrifugation well from the outer blood injection hole, and a cover integrally attached to the outer blood injection hole to open and close the outer blood injection hole,
   wherein the cover is hung on a strip extending inward in the radius direction, and a corrugated part is formed on the strip in a horizontal direction, and
   the cover further includes a reinforcing lip inserted into the outer blood injection hole on the inside thereof and a coupling lip coupled to coupling holes formed on the left and right sides of the outer blood infection hole.

2. The cartridge capable of the centrifugation and the automatic analysis of claim 1, wherein
   there are ten areas on the cartridge that are weight-balanced based on the mass center of the centrifugation well, at least two or more sample wells have a cross-section formed as a long rectangle in the radius direction, the centrifugation well has the ⅔ length of the long side of at least two or more sample wells and has a trapezoid cross-section of which an outer circumference side is longer than the inner circumference, and a reagent well has a circular cross-section, but becomes narrower toward the bottom.

3. The cartridge capable of the centrifugation and the automatic analysis of claim 1, wherein
   the circular plate includes a cylinder-shaped supporting plate in which a rotation driving unit is coupled at the center thereof, a center hole disposed when the cover opens the outer blood injection hole and a coupling hole that is spaced and disposed near the center hole with a predetermined interval and is coupled with the coupling protrusion of the rotation driving unit are spaced and disposed with a predetermined interval, and at least two or more of the sample well, the centrifugation well, a fluorescent material well, and the tip receiving well are connected and supported at the bottom along the circumference of the circular plate.

4. The cartridge capable of the centrifugation and the automatic analysis of claim 1, wherein
   the height facing the inner blood injection hole formed on the vertical inner wall of the centrifugation well is displayed on the vertical outer wall, and the position of the inner blood injection hole is set such that the cartridge is weight balanced.

5. The cartridge capable of the centrifugation and the automatic analysis of claim 1, wherein
   one of a reagent well and a fluorescent material well is configured of an opaque section, the fluorescent material well has a flat bottom, and a position mark connected to the upper end of the fluorescent material well is formed on the circular plate.

6. The cartridge capable of the centrifugation and the automatic analysis of claim 1, wherein
   a sealing edge part is formed along the upper opening of the at least two of more sample well, the centrifugation well and a reagent well, the sealing edge part includes an interior circumference connection part, a radius direction connection part, an exterior circumference connection part, and a vent hole formed by separating the exterior circumference connection part, and a foil film is coupled for the sealing edge part to block the upper openings.

* * * * *

UNITED STATES PATENT AND TRADEMARK OFFICE
CERTIFICATE OF CORRECTION

PATENT NO. : 12,158,477 B2
APPLICATION NO. : 17/284958
DATED : December 3, 2024
INVENTOR(S) : Jin et al.

Page 1 of 1

It is certified that error appears in the above-identified patent and that said Letters Patent is hereby corrected as shown below:

In the Claims

Column 9,
Line 52, "infection" should read --injection--.

Column 10,
Line 44, "at least two of more sample well" should read --at least two or more of the sample well--.

Signed and Sealed this
Eleventh Day of February, 2025

Coke Morgan Stewart
*Acting Director of the United States Patent and Trademark Office*